United States Patent [19]

Pereira et al.

[11] Patent Number: 5,607,916
[45] Date of Patent: Mar. 4, 1997

[54] METHOD AND COMPOSITION FOR THE TREATMENT OF SEPTIC SHOCK

[75] Inventors: Heloise A. Pereira, Oklahoma City; Daniel J. Brackett, Seminole; Megan R. Lerner, Shawnee, all of Okla.

[73] Assignee: The Board of Regents of the University of Oklahoma, Norman, Okla.

[21] Appl. No.: 235,399

[22] Filed: Apr. 29, 1994

Related U.S. Application Data

[63] Continuation-in-part of Ser. No. 969,931, Oct. 30, 1992, Pat. No. 5,458,874, which is a continuation of Ser. No. 855,417, Mar. 19, 1992, Pat. No. 5,484,885, which is a continuation-in-part of Ser. No. 543,151, Jun. 25, 1990, abandoned, which is a continuation-in-part of Ser. No. 375,739, Jul. 5, 1989, abandoned.

[51] Int. Cl.$^6$ .......................... A61K 38/10; A61K 38/16; C07K 7/00; C07K 14/00
[52] U.S. Cl. .................... 514/12; 514/2; 514/10; 514/11; 514/21; 530/300; 530/325; 530/326
[58] Field of Search .......................... 514/12, 11, 21, 514/10

[56] References Cited

U.S. PATENT DOCUMENTS

| | | | |
|---|---|---|---|
| 5,087,569 | 2/1992 | Gabay et al. | 435/212 |
| 5,126,257 | 6/1992 | Gabay et al. | 435/212 |
| 5,171,739 | 12/1992 | Scott | 514/12 |
| 5,234,912 | 8/1993 | Marra et al. | 514/21 |
| 5,308,834 | 5/1994 | Scott et al. | 514/12 |
| 5,338,724 | 8/1994 | Gabay et al. | 514/12 |
| 5,458,874 | 10/1995 | Pereira et al. | 424/85.1 |
| 5,485,885 | 1/1996 | Pereira et al. | 530/326 |

OTHER PUBLICATIONS

EMBASE No: 95085016, Hurley, J. C. 1995. Endotoxaemia and novel therapies for the treatment of sepsis, Expert Opinion on Investigational Drugs (United Kingdom), vol. 4, Number 3, pp. 163–174.

EMBASE No: 94208915, Rogy et al. 1994. Anti–endotoxin therapy in primate bacteremia with HA–1A and BPI ANN. SURG. (USA), vol. 220, Number 1, pp. 77–85.

Cross et al., Jul. 1993. Infection and Immunity, vol. 61, Number 7, pp. 2741–2747.

DIALOG(R)File 155 accession number 93226936, Offenstadt, G. et al. Jan. 1, 1993, Therapeutic perspectives of severe infectious states, Rev Prat (FRANCE), vol. 43, Number 1, pp. 59–64.

Ziegler et al., "Treatment of Gram–Negative Bacteremia and Shock with Human Antiserum To A Mutant *Escherichia Coli*", *The New England Journal of Medicine*, vol. 307, No. 20, Nov. 11, 1982.

Baumgartner et al., "Prevention of Gram–Negative Shock and Death In Surgical Patients By Antibody to Endotoxin Core Glycolipid", *The Lancet*, Jul. 13, 1985, pp. 59–63.

Brackett et al., "Evaluation of Cardiac Output, Total Peripheral Vascular Resistance, and Plasma Concentrations of Vasopressin in the Conscious, Unrestrained Rat During Endotoxemia", *Circulatory Shock*, 17:273–284, 1985.

Fisher et al., "Initial Evaluation of Human Monoclonal Anti–Lipid A Antibody (HA–1A) in Patients with Sepsis Syndrome", *Critical Care Medicine*, vol. 18, No. 12, 1990, 1311–1315.

(List continued on next page.)

*Primary Examiner*—Robert A. Wax
*Assistant Examiner*—William W. Moore
*Attorney, Agent, or Firm*—Dunlap & Codding, P.C.

[57] ABSTRACT

The present invention contemplates a composition and method for treating septic shock in a mammal or as a prophylactic treatment prior to a surgical procedure, comprising administering a therapeutically effective amount of a bacterial lipopolysaccharide binding peptide derived from CAP37 protein. In a preferred version, the composition and method of use may comprise a peptide comprising amino acids 20–44 of CAP37 or a subunit thereof.

6 Claims, 11 Drawing Sheets

SYSTEMIC VASCULAR RESISTANCE

OTHER PUBLICATIONS

Greenman et al., "A Controlled Clinical Trial of E5 Murine Monoclonal IgM Antibody to Endotoxin in the Treatment of Gram–Negative Sepsis", *JAMA*, vol. 266, No. 8, Aug. 28, 1991, pp. 1097–1102 and 1125–1126.

J. Johnston, "Molecular Science Sets Its Sights on Septic Shock", *The Journal of NIH Research*, vol. 3, Oct. 1991, pp. 61–65.

Ziegler et al., "Treatment of Gram–Negative Bacteremia and Septic Shock With HA–1A Human Monoclonal Antibody Against Endotoxin", *The New England Journal of Medicine*, vol. 324, No. 7, Feb. 14, 1991, pp. 429–436

"Anti–Endotoxin Monoclonal Antibodies", various editorials, *The New England Journal of Medicine*, vol. 327, No. 12, Sep. 17, 1992, pp. 889–890.

C. Welbourn and Y. Young, "Endotoxin, Septic Shock and Acute Lung Injury: Neutrophils, Macrophages and Inflammatory Mediators", *Br. J. Surg.*, vol. 79, Oct. 1992, pp. 998–1003.

W. Ammons and A. Kung, "Recombinant Amino Terminal Fragment of Bactericidal/Permeability–Increasing Protein Prevents Hemodynamic Responses to Endotoxin", *Circulatory Shock*, 41:176–184, 1993.

Pereira et al., "Synthetic Bactericidal Peptide Based on CAP37: A 37kDa Human Neutrophil Granule–Associated Cationic Antimicrobial Protein Chemotactic for Monocytes", *Proc. Natl. Acad. Sci. USA*, vol. 90, pp. 4733–4737, May 1993.

S. Aldridge, "Meeting the Challenge of Sepsis", *TIBTECH*, vol. 11, Sep. 1993.

W. Hoffman, and C. Natanson, "Endotoxin in Septic Shock", *Anesth Analg*, 1993:77:613–24.

Stewart et al., "Comparison of *Staphylococcus aureus* and *Escherichia coli* Infusion in Conscious Rats", *Journal of Surgical Research*, 56, 60–66, 1994.

J. Gabay, "Ubiquitous Natural Antibiotics" *Science*, vol., 264, 15 Apr. 1994, pp. 373–374.

METHOD AND COMPOSITION FOR THE TREATMENT OF SEPTIC SHOCK

Some aspects of this invention were made in the course of Grant AI 28018 awarded by the National Institutes of Health and therefore the Government has certain rights in some aspects of this invention.

CROSS REFERENCE TO RELATED APPLICATIONS

This application is a continuation-in-part of U.S. patent application Ser. No. 07/969,931, filed Oct. 30, 1992, issued as U.S. Pat. No. 5,458,874 on Oct. 17, 1995, which is a continuation of U.S. Ser. No. 07/855,417, filed Mar. 19, 1992, issued as U.S. Pat. No. 5,484,885 on Jan. 16, 1996, which is a continuation-in-part of U.S. Ser. No. 07/543,151, filed Jun. 25, 1990, now abandoned which is a continuation-in-part of U.S. Ser. No. 07/375,739, filed Jul. 5, 1989, now abandoned. The specification and sequence listing of each of the above applications is hereby incorporated herein by reference.

BACKGROUND

Septic shock (also known as sepsis) causes more than 150,000 deaths annually in the United States. Sepsis is defined as a clinical disorder whose symptoms may include well defined abnormalities in body temperature, heart rate, breathing rate, white blood cell count, hypotension, organ perfusion abnormalities, and multiple organ dysfunction. It may be caused by bacterial (either gram negative or gram positive), fungal, viral and other infections as well as by non-infective stimuli such as multiple trauma, severe burns, organ transplantation and pancreatitis. In Europe there are 500,000 cases annually with a lethal outcome of 40–70%. Even with improved patient management the mortality rate ranges from 50% to 75% in patients with established septic shock. There has not been a significant decrease in this mortality rate since the advent of broad spectrum antibiotics in the early 1960s. Septic patients usually die as a result of poor tissue perfusion and injury followed by multiple organ failure. It is now generally accepted that a significant portion of the peripheral responses occurring during septic shock are initiated by endotoxin. Endotoxin (also referred to herein as lipopolysaccharide, bacterial lipopolysaccharide or LPS), an outer membrane component of gram-negative bacteria, is released upon the death or multiplication of the bacteria. Administration of endotoxin to experimental animals elicits a series of sequential cardiovascular, metabolic, and pathologic responses culminating in organ dysfunction and failure, ultimately resulting in death. When endotoxin is administered to normal human subjects, physiologic, biochemical, and cellular responses are induced that quantitatively mimic those occurring during septic shock. However, it is becoming increasingly recognized that the majority of responses observed during sepsis and endotoxemia are not due to direct actions of endotoxin, but result from endotoxin induction of a myriad of cellular and humoral inflammatory mediators. Furthermore, even with the vast research and clinical literature regarding sepsis and endotoxemia, there is no definitive regimen for the treatment of septic shock with the thrust of therapy being targeted at correction of symptoms.

Clinicians are dissatisfied with the existing therapies for septic shock which currently consist of antibiotic therapy or hemodynamic and metabolic support. The intravenous antibiotics eradicate the bacteria and the fluid infusion attempts to reverse the hypotension.

The impact of sepsis and any situation of endotoxemia is particularly devastating to patients with compromised cardiac and hepatic function and to immunocompromised patients. Patients at high risk are the elderly (an increasing percentage of our society), chemotherapy patients, and those requiring surgery or invasive instrumentation. The current therapy of antibiotics and hemodynamic support has not proven to be successful. Experimental studies have indicated that antibodies to certain cytokines may ameliorate some, but not all of the manifestations of the sepsis syndrome. There is such an explosion of physiological responses and release of mediators during septic shock that the antagonism of a single mediator may not always be effective.

Although septic shock can follow any bacterial infection, it is most often the sequel to a gram negative infection. Klebsiella, Pseudomonas, *Escherichia coli*, Bacteroides and Salmonella are the most frequent cause.

Septic shock usually begins with tremor, fever, falling blood pressure, rapid breathing and heart beat, and skin lesions. Within hours or days it can progress to spontaneous clotting in the blood vessels, severe hypotension, multiple organ failure and death.

Most of the damage comes not from the invading bacteria but from endotoxin. The component responsible for the toxic effect of the LPS molecule is the lipid component, called lipid A. This region is buried in the outer membrane of the bacterium and is believed to be reasonably constant between different species of gram negative bacteria. The polysaccharide region of the molecule extends from the surface of the bacterium and is different for each bacterial strain. The polysaccharide region consists of an inner core region composed of a heptose, and a 3, deoxy-D-manno-2-octulosonic acid (KDO) molecule. The KDO molecule is found in all lipopolysaccharide and links the polysaccharide to the lipid A moiety.

The manner in which endotoxin evokes its effects is by binding to cells such as monocytes/macrophages or endothelial cells, and triggering them to produce various mediator molecules such as toxic oxygen radicals, hydrogen peroxide, tumor necrosis factor-alpha (TNF-$\alpha$), various interleukins (IL-1, IL-6, and IL-8). Endotoxin in even the very smallest amounts can activate these cells.

Depending on the dose or concentration of endotoxin, the effects may either be deleterious or advantageous to the host. If excessive TNF-$\alpha$, IL-1, IL-6, and IL-8 are produced, they can evoke endotoxic (or septic) shock with symptoms ranging from chills and fever to circulatory failure, multiorgan failure, and death. An improved method of treating or preventing septic shock would be of great value.

DESCRIPTION OF THE INVENTION

Figure 1:
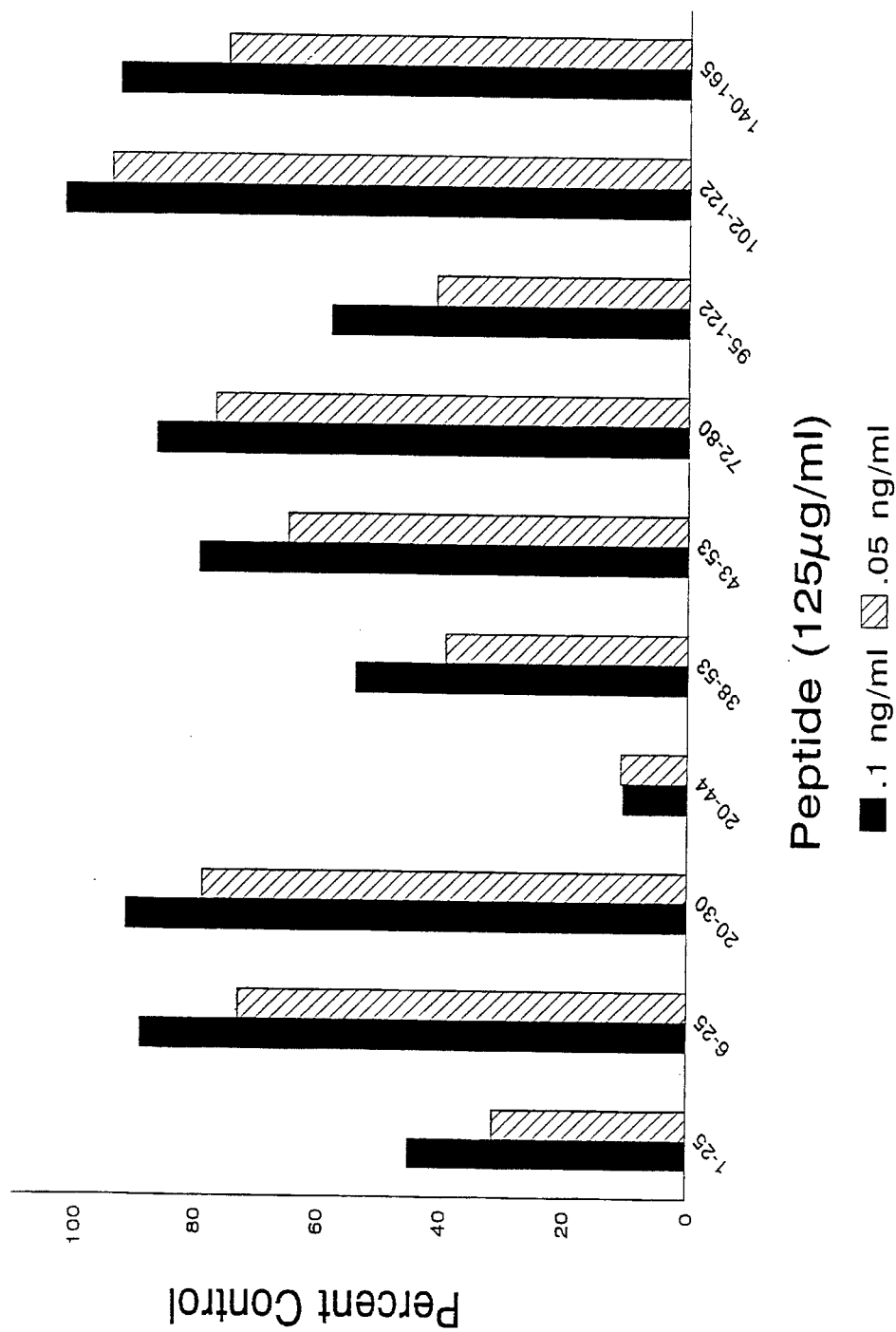
FIG. 1 is a graph comparing the effects of various CAP37 peptides on the neutralization of lipid A.

A naturally occurring protein called CAP37 (Cationic Antimicrobial Protein having a molecular weight of 37 kD) has been shown to be a multifunctional protein, with extremely important functions in host defense and inflammation. Not only does CAP37 have antibiotic activity but it is also a very potent chemoattractant for monocytes, can bind heparin, and has the capacity to bind endotoxin or lipopolysaccharide. The protein can be isolated from human neutrophils and is present in the granules of those cells. It has been purified to homogeneity, and it migrates on SDS-PAGE as a 37 kD protein. Further details of the amino acid sequence and purification of the protein and peptides derived from the protein can be found in copending U.S. Ser. No. 07/969,931, filed Oct. 30, 1992 and in the article "Synthetic Bacterial Peptide Based On CAP37: A 37-kDa Human Neutrophil Granule-Associated Cationic Antimicrobial Protein Chemotactic For Monocytes", H. A. Pereira, I. Erdem, J. Pohl, and J. Spitznagel, *Proc. Natl. Acad. Sci. USA*, 90:4733–4737, May 1993, which is hereby incorporated herein by reference.

The present invention contemplates a composition for treating septic shock in a mammal, comprising a therapeutically effective amount of a peptide derived from CAP37 protein. In a preferred version, the composition may comprise a peptide having the amino acid sequence as defined in the Sequence Listing of SEQ ID NO:1. In another version of the invention, the composition may comprise a peptide comprising a subunit of the amino acid sequence defined in the Sequence Listing of SEQ ID NO:1, for example, having the amino acid sequence as defined in the Sequence Listing of SEQ ID NO:2.

The invention further contemplates a peptide capable of binding to bacterial lipopolysaccharide, comprising the amino acid sequence as defined in the Sequence Listing of SEQ ID NO:1 or an effective subunit thereof. The invention further contemplates a DNA molecule comprising a DNA sequence coding for a peptide derived from the 20th to 44th amino acid region of CAP37 as defined in the Sequence Listing by SEQ ID NO:1, or an effective subunit thereof, the peptide coded therefor effective in binding to bacterial lipopolysaccharide.

The invention further contemplates a method for treating septic shock in a mammal, comprising administering to the mammal a therapeutic composition comprising a pharmacologically effective amount of a bacterial lipopolysaccharide binding peptide derived from CAP37 protein (the term "bacterial lipopolysaccharide binding peptide" when used herein is meant to refer to a peptide derived from CAP37 protein and is not meant to be confused with the polypeptide known in the art as "Lipopolysaccharide Binding Protein"). In a preferred embodiment of the method, the peptide derived from CAP37 has the amino acid sequence as defined in the Sequence Listing by SEQ ID NO:1 or an effective subunit thereof. In an alternate embodiment of the method, the peptide derived from CAP37 has the amino acid sequence as defined in the Sequence Listing by SEQ ID NO:2.

The invention further contemplates a method of prophylactic treatment for preventing septic shock in a mammal, comprising administering to the mammal a therapeutic composition comprising a pharmacologically effective amount of a lipopolysaccharide binding peptide derived from CAP37 protein. In a preferred embodiment of the method, the peptide derived from CAP37 has the amino acid sequence as defined in the Sequence Listing by SEQ ID NO:1. In an alternate version of the invention, the peptide derived from CAP37 has the amino acid sequence as defined in the Sequence Listing by SEQ ID NO:2.

The present invention further contemplates a method of treating physiological effects induced by bacterial lipopolysaccharide in a mammal, for example on systemic vascular resistance, cardiac output, tissue perfusion, and white blood cell count, comprising administering to the mammal a therapeutic composition comprising a pharmacologically effective amount of a bacterial lipopolysaccharide binding peptide derived from CAP37 protein. In a preferred embodiment of the method, the peptide derived from CAP37 has the amino acid sequence as defined in the Sequence Listing by SEQ ID NO:1. In an alternate version of the invention, the peptide derived from CAP37 has the amino acid sequence as defined in the Sequence Listing by SEQ ID NO:2.

The present invention further contemplates a method of mediating or preventing the effects of a bacterial comprising lipopolysaccharide-induced response in a test animal, the steps of providing a test animal, administering a predetermined amount of endotoxin to the test animal, and administering a predetermined amount of CAP37 peptide 20–44 to the test animal.

ANTIBIOTIC ACTIVITY OF CAP37 PEPTIDE 20–44

Some of the results of Pereira, et al. 1993 are summarized below. A peptide NQGRHFCGGALIHARFVMTAASCFQ corresponding to residues 20–44 of the mature CAP37 protein has been shown to have strong antimicrobial activity (for the sequence of peptide 20–44, see Seq. ID No. 1 of the present application which corresponds to Seq. ID No. 8 in U.S. Ser. No. 07/969,931). Various overlapping peptides corresponding to the amino acid sequences 1–25, 20–44, 38–53, 43–53, 72–80, 95–122, 102–122, 113–122, 130–146, and 140–165 of the native CAP37 protein were synthesized. All peptides were assayed for bactericidal activity using *Salmonella typhimurium* SH9178 as the test organism. It was apparent that one of the peptides, peptide 20–44, had significantly greater antibiotic activity than the other peptides tested (FIG. 1 in Peteira et al., 1993). Almost one hundred percent (99.3%) of the bacteria were killed at the highest concentration tested and 90% of killing was achieved at 100 ug/ml concentration of the peptide. Various substitutions and truncations of peptide 20–44 indicated that peptide 20–44 was by far the most active. Particularly interesting was an analog of peptide 20–44 in which the cysteines at positions 26 and 42 were substituted with serines. This serine-substituted peptide was inactive in our bactericidal assays.

As noted above, the present invention is a method for using a composition comprising a CAP37 peptide in the treatment of sepsis. The use of CAP37 peptide 20–44 would not only be confined to patients who had already developed endotoxemia, but could also be used prophylactically before any bowel or bladder surgery or manipulations of other organs where gram negative bacteria normally reside and create the risk of entry into the bloodstream and the subsequent induction of sepsis. The present invention also contemplates using CAP37 peptide 23–42, a subunit of peptide 20–44, in the treatment of sepsis (for the sequence of peptide 23–42, see Seq. ID No. 2 in the present application, which corresponds to Seq. ID No. 7 in U.S. Ser. No. 07/969,931).

Bactericidal Activity of CAP37 Peptide 20–44 Against Various Bacterial Strains

Figure 2:
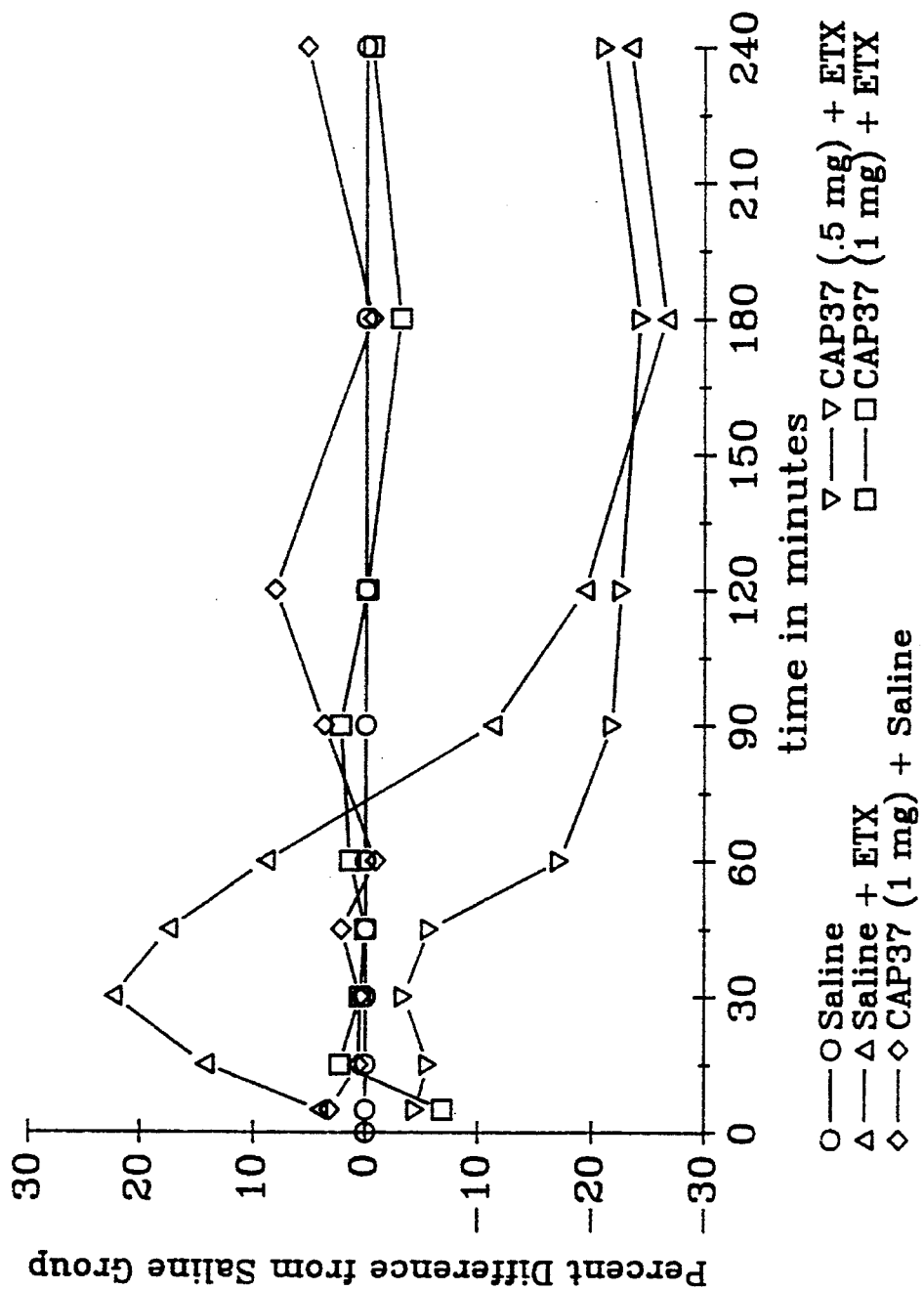
FIG. 2 is a graph comparing the effects of endotoxin and CAP37 peptide 20–44 on cardiac index in the hyperdynamic model of septic shock.

The bactericidal activity of peptide 20–44 was evaluated against a number of gram negative and gram positive bacteria (FIG. 14 in U.S. Ser. No. 07/855,417) and against various strains of *Salmonella typhimurium* with a range of endotoxin chemotypes and various clinical isolates of *S. typhimurium* designated with the prefix C (FIG. 2 in Pereira et al., 1993). Of the various organisms tested, *Pseudomonas aeruginosa, Escherichia coli,* and *Enterococcus faecalis* were highly sensitive to the action of CAP37. Significantly, peptide 20–44 has enhanced bactericidal activity compared to the native CAP37 protein. Previous evidence strongly indicated native CAP37 has a fairly narrow spectrum of bactericidal activity, being primarily effective against gram negative bacteria such as *S. typhimurium, E. coli, P. aeruginosa, S. typhi,* and *Shigella sonnei*. Most interestingly the activity of peptide 20–44 is not limited in its action to gram negative bacteria alone. It is particularly active against *E. faecalis* and shows moderate activity against *Staphyloccus aureus*, which is resistant to native CAP37. Other gram positive organisms such as *Listeria monocytogenes* and *Streptococcus pyogenes* are resistant to the activity of the 20–44 peptide. All strains of Proteus tested and *Morganella morganii* are resistant to the peptide 20–44. The moderate activity of peptide 20–44 against *S. aureus* indicates that it may be useful in treating septic shock caused by *S. aureus* and possibly other gram positive bacteria.

The microbicidal activity of peptide 20–44 parallels the activity of the native CAP37 protein regarding the effect on various strains of *S. typhimurium* with a range of LPS chemotypes. In general, the smooth strains of Salmonella are more resistant and the rough strains more sensitive. A polymyxin B resistant strain (pmrA) of Salmonella (SH7426) was cross resistant to peptide 20–44 as it was to CAP37. Resistance to peptide 20–44 conferred by pmrA compensated remarkably well for the decrease in resistance due to rough, Rb chemotype due to the rfaJ mutation. The six clinical isolates of *S. typhimurium* showed various levels of sensitivity.

Thus, there is substantial data that peptide 20–44 mimics the potent antimicrobial activity of the native protein CAP37 but appears to have a broader spectrum of action since it is also active on gram positive organisms. Peptide 20–44 is antimicrobial at concentrations of $1.25-7.5\times10^{-5}$, as are other antibiotic peptides such as the defensins. Peptide 20–44 appears to be maximally active between pH 5 and pH 5.5. The two cysteine residues at positions 26 and 42 are required for bactericidal activity suggesting that disulfide bond formation may be important for antimicrobial action. Analysis of the activity of several related peptides indicates that a combination of features such as hydrophobicity (56% of its amino acid residues are hydrophobic), basic charge, and relatively small size facilitates its interaction with lipid A on the surface of gram negative organisms, and may be the basis for its antibacterial activity.

Lipopolysaccharide Binding Activity of CAP37

Native CAP37 binds to endotoxin. An ELISA was used to determine binding of native CAP37 to various preparations of LPS and lipid A. The microtitre plate was coated with LPS from *S. minnesota* wild type, LPS from *S. minnesota* Re mutant, lipid A from *S. minnesota* wild type R595, and lipid A from *S. typhimurium* Re mutant at concentrations ranging from 0 to 50 µg/ml and incubated overnight. After careful washing, the plates were incubated with 120 ng per well of CAP37. A monospecific rabbit anti CAP37 antibody was then applied to the plates, and development of the ELISA was performed as previously published in Peteira, et al., "Quantitation of a Catonic Antimicrobial Granule Protein of Human Polymorphonuclear Leukocytes by ELISA", *J. Immuno. Methods*, 117:115–120, 1989 which is hereby incorporated herein by reference. The results described therein support the hypothesis that CAP37 is able to bind endotoxin, and in particular the lipid A moiety.

Lipopolysaccharide Neutralization and Binding by CAP37 and Peptide 20–44

Figure 8:
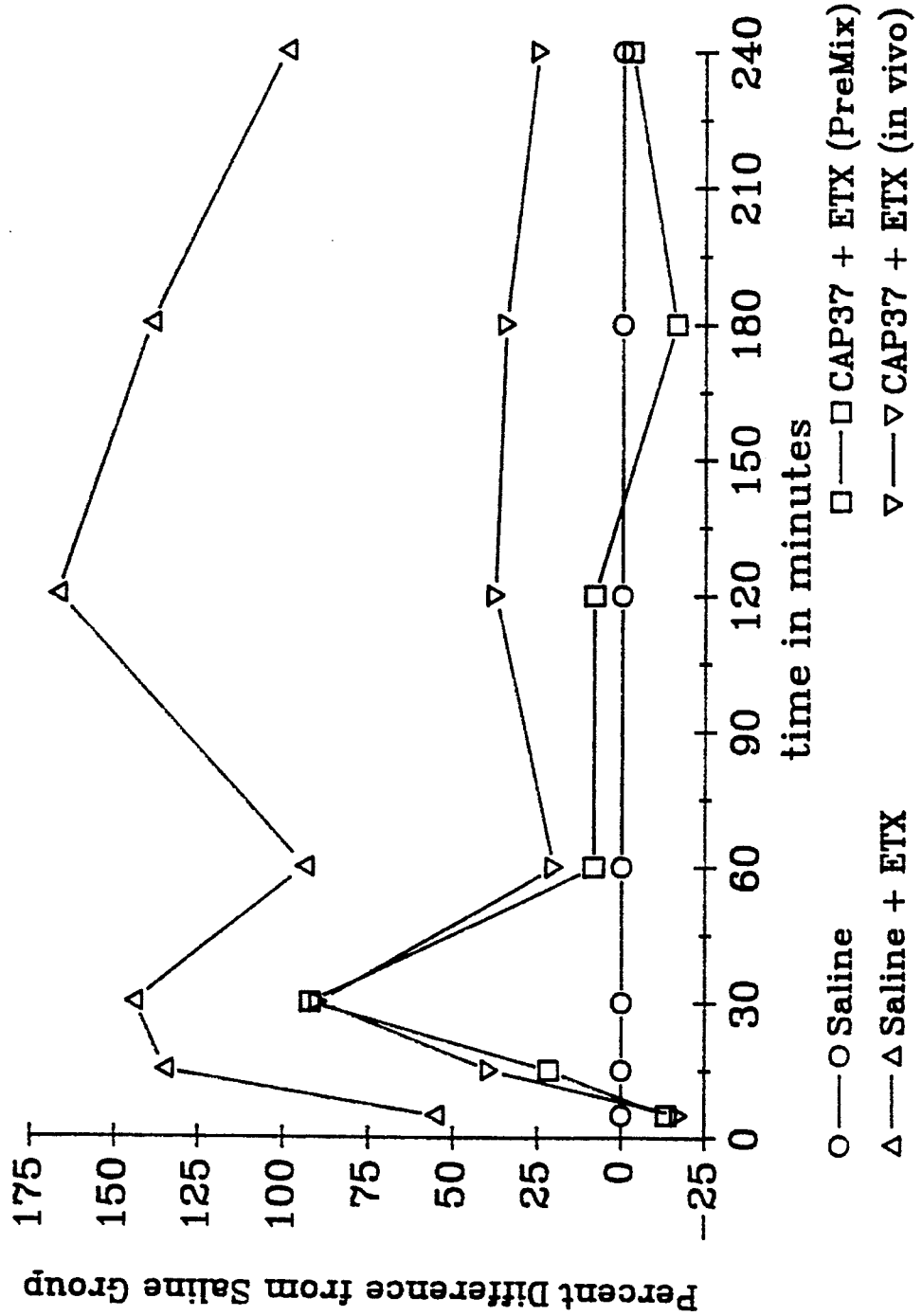
FIG. 8 is a graph comparing the effects of endotoxin and CAP37 peptide 20–44 on systemic vascular resistance in the hypodynamic model of septic shock.
Figure 9:
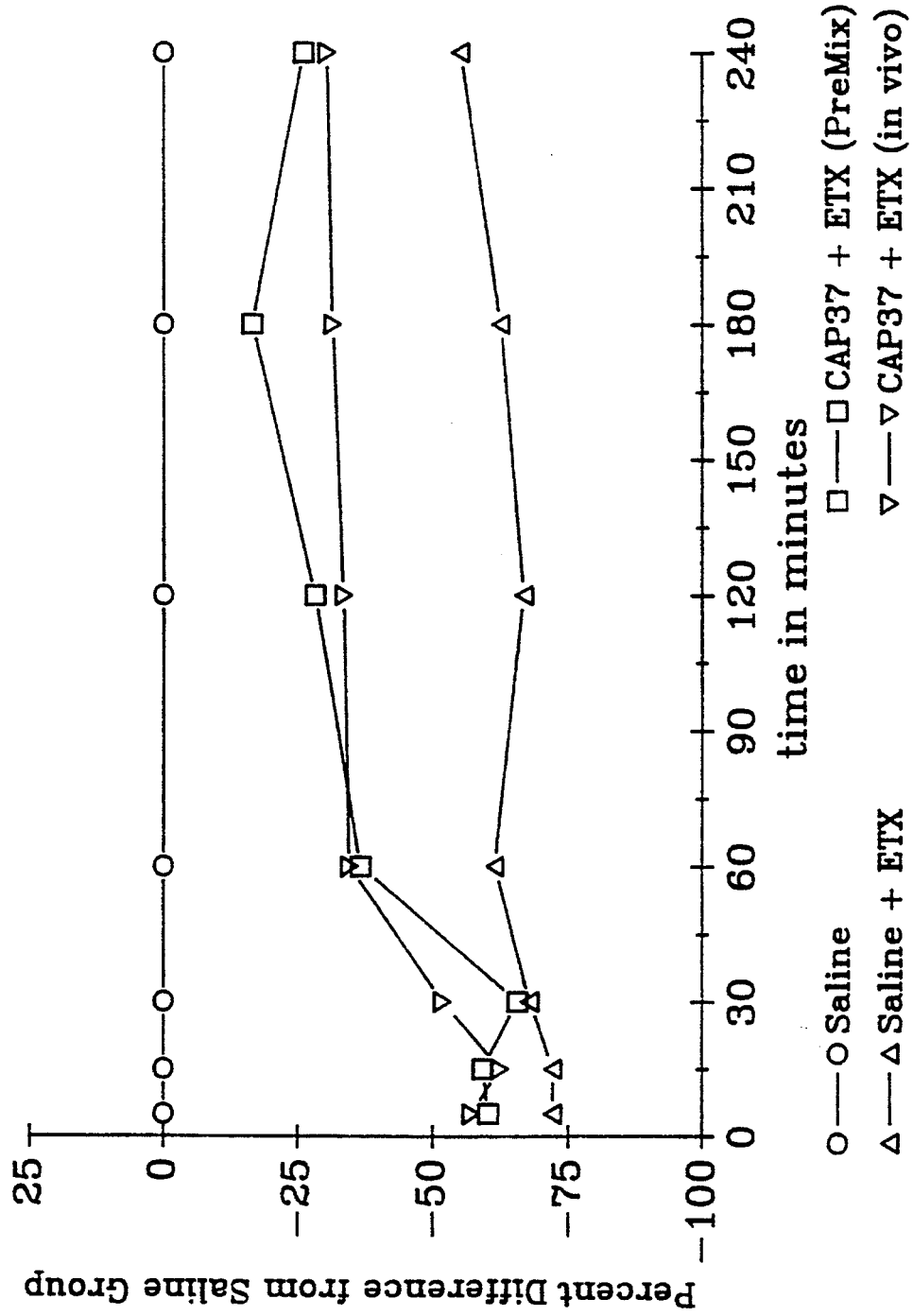
FIG. 9 is a graph comparing the effects of endotoxin and CAP37 peptide 20–44 on cardiac stroke volume in the hypodynamic model of septic shock.

It was found that the bactericidal action of CAP37 peptide 20–44 could be inhibited by preincubating the peptide with either LPS or lipid A. These results strongly suggest that CAP37 peptide 20–44 is also the domain responsible for endotoxin binding (FIG. 8 in Pereira, et al., 1993). Further confirmation that CAP37 peptide 20–44 binds endotoxin was obtained from independent means other than inhibition of bactericidal activity. The chromogenic Limulus amebocyte lysate (LAL) assay indicated that CAP37-peptide 20–44 significantly neutralized monophosphoryl lipid A (See FIG. 1). FIG. 1 shows results indicating the neutralization of monophosphoryl lipid A by CAP37 peptides. Quantities of 125 µg/ml of CAP37 peptides 1–25, 6–25, 20–30, 20–44, 38–53, 43–53, 72–80, 95–122, 102–122, and 140–165 were incubated with 0.1 ng/ml and 0.05 ng/ml of monophosphoryl lipid A. Of all of the peptides tested, peptide 20–44 had the most significant degree of neutralization of lipid A. The experiments demonstrating that endotoxin inhibits the bactericidal action of the peptide, together with results showing that other peptides based on the CAP37 native sequence are unable to neutralize LPS, cause us to hypothesize that the antibacterial domain is also the lipid A binding domain of CAP37. Moreover, it has been shown that *S. typhimurium* resistant to polymyxin B are cross resistant to CAP37.

The major benefit of using CAP37 peptide 20–44 over other systems that may block deleterious effects of endotoxin is that the functional binding domain of CAP37 is narrowed down to a 25 amino acid polypeptide. This is a considerable reduction in size from Bactericidal Permeability-Increasing Protein (BPI) and Lipopolysaccharide Binding Protein (LBP), making it more membrane permeable, and less demanding to produce synthetically. Further, the antibacterial activity of BPI is directed solely against gram negative bacteria while data discussed herein indicates that CAP37 peptide 20–44 is active against certain gram positive bacteria as well as gram negative bacteria.

ATTENUATION OF ENDOTOXIN EFFECTS IN VIVO

Hyperdynamic Model

Figure 3:
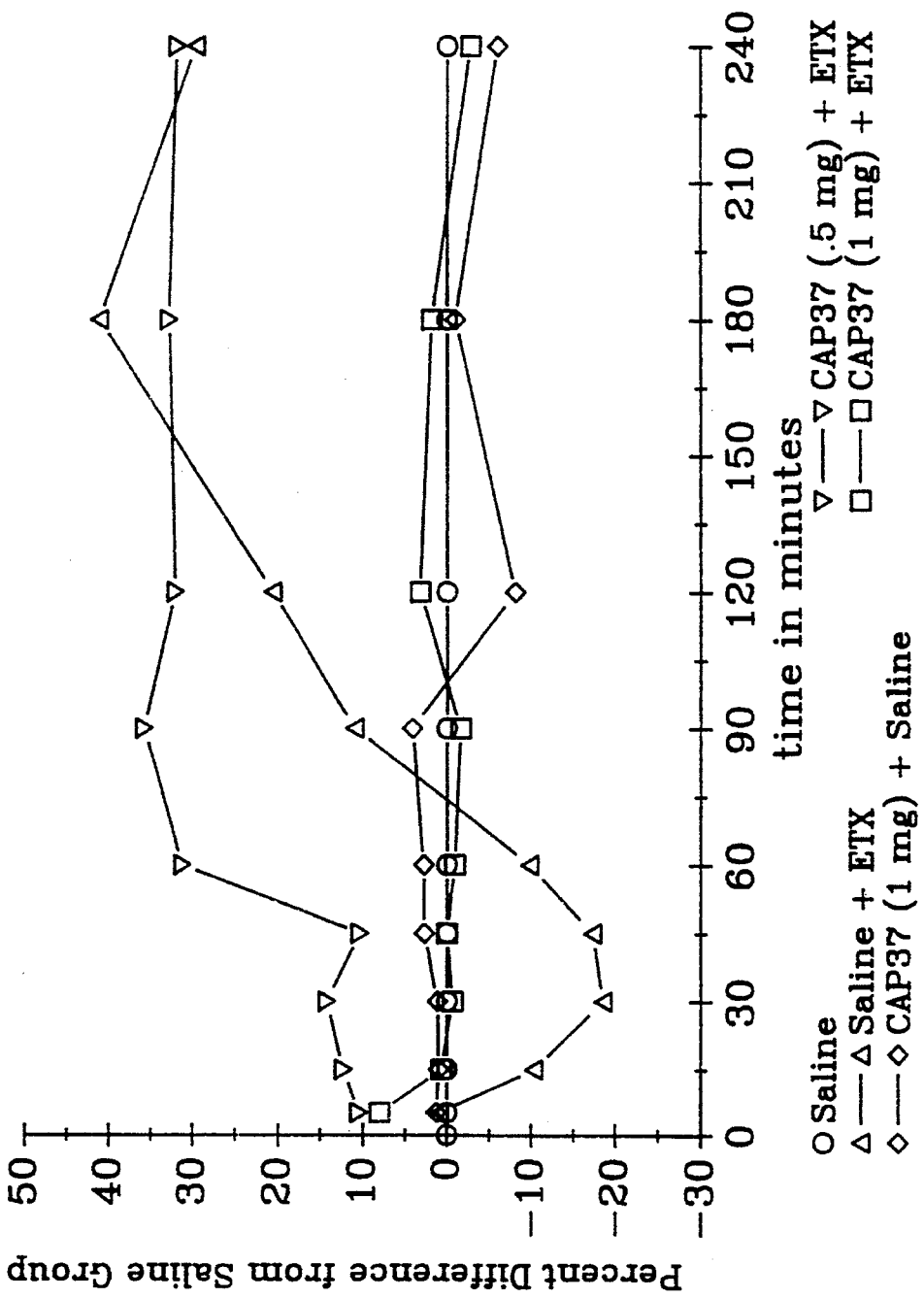
FIG. 3 is a graph comparing the effects of endotoxin and CAP37 peptide 20–44 on systemic vascular resistance in the hyperdynamic model of septic shock.
Figure 4:
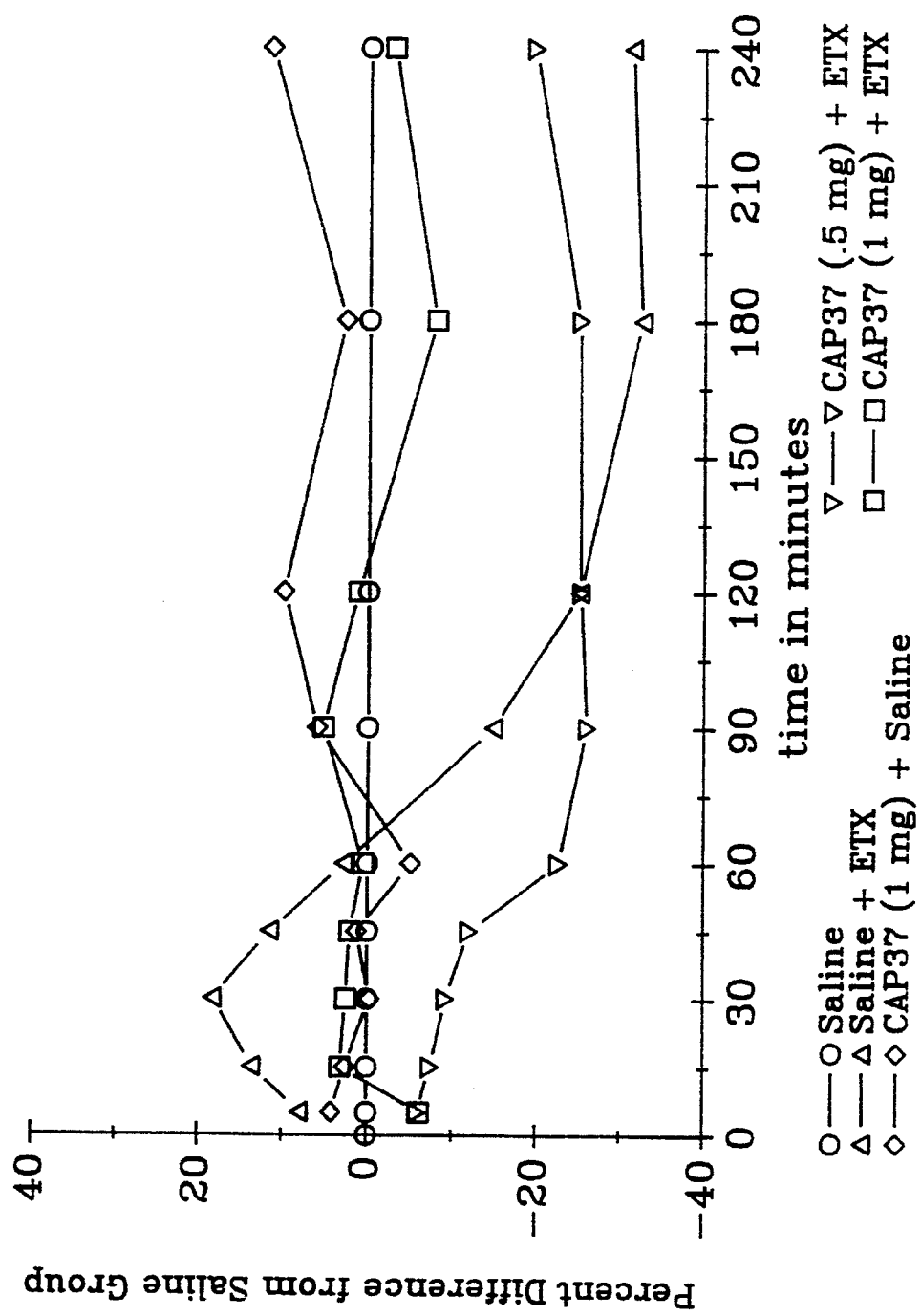
FIG. 4 is a graph comparing the effects of endotoxin and CAP37 peptide 20–44 on cardiac stroke volume in the hyperdynamic model of septic shock.
Figure 5:
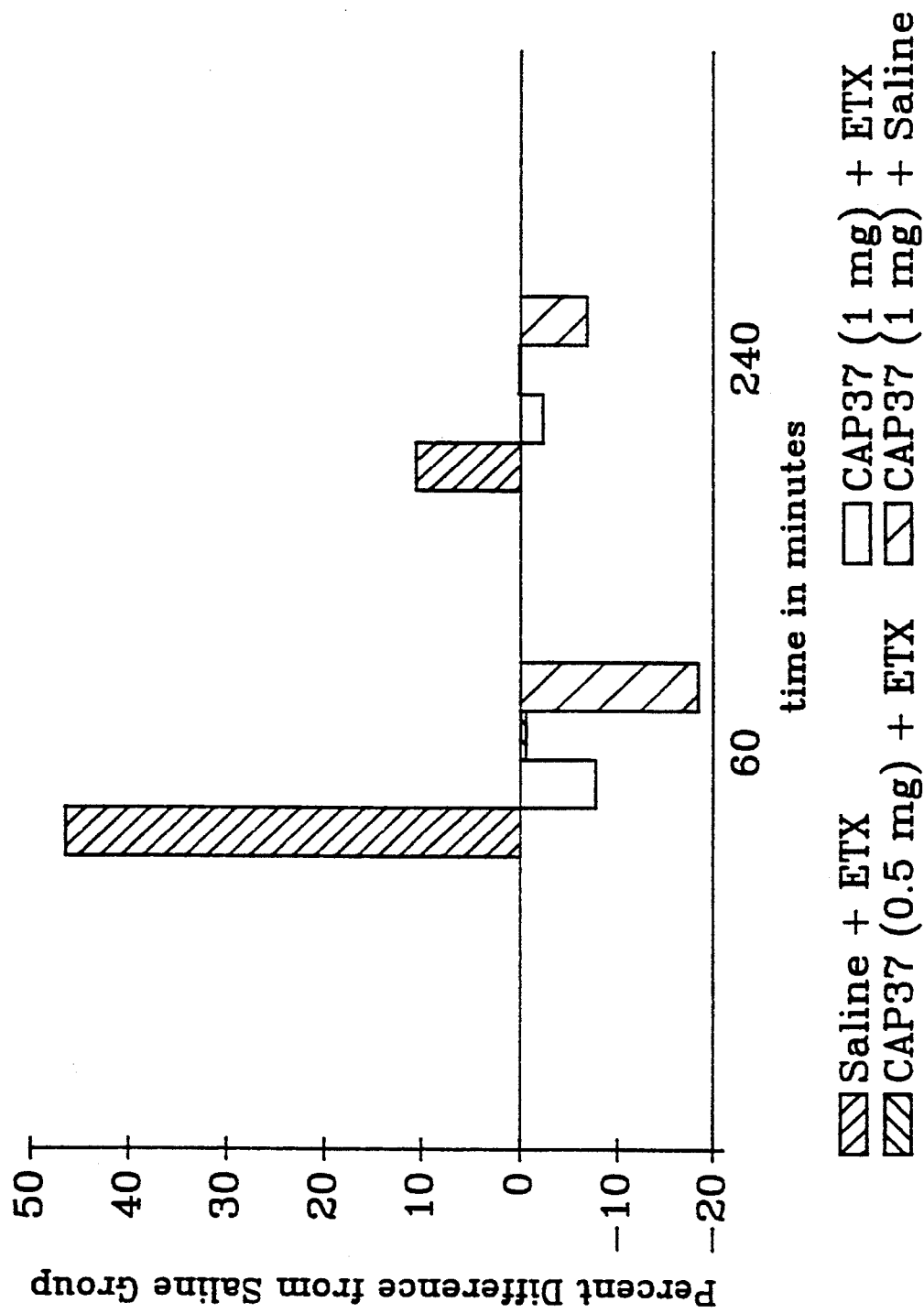
FIG. 5 is a graph comparing the effects of endotoxin and CAP37 peptide 20–44 on lactate concentration in the hyperdynamic model of septic shock.
Figure 6:
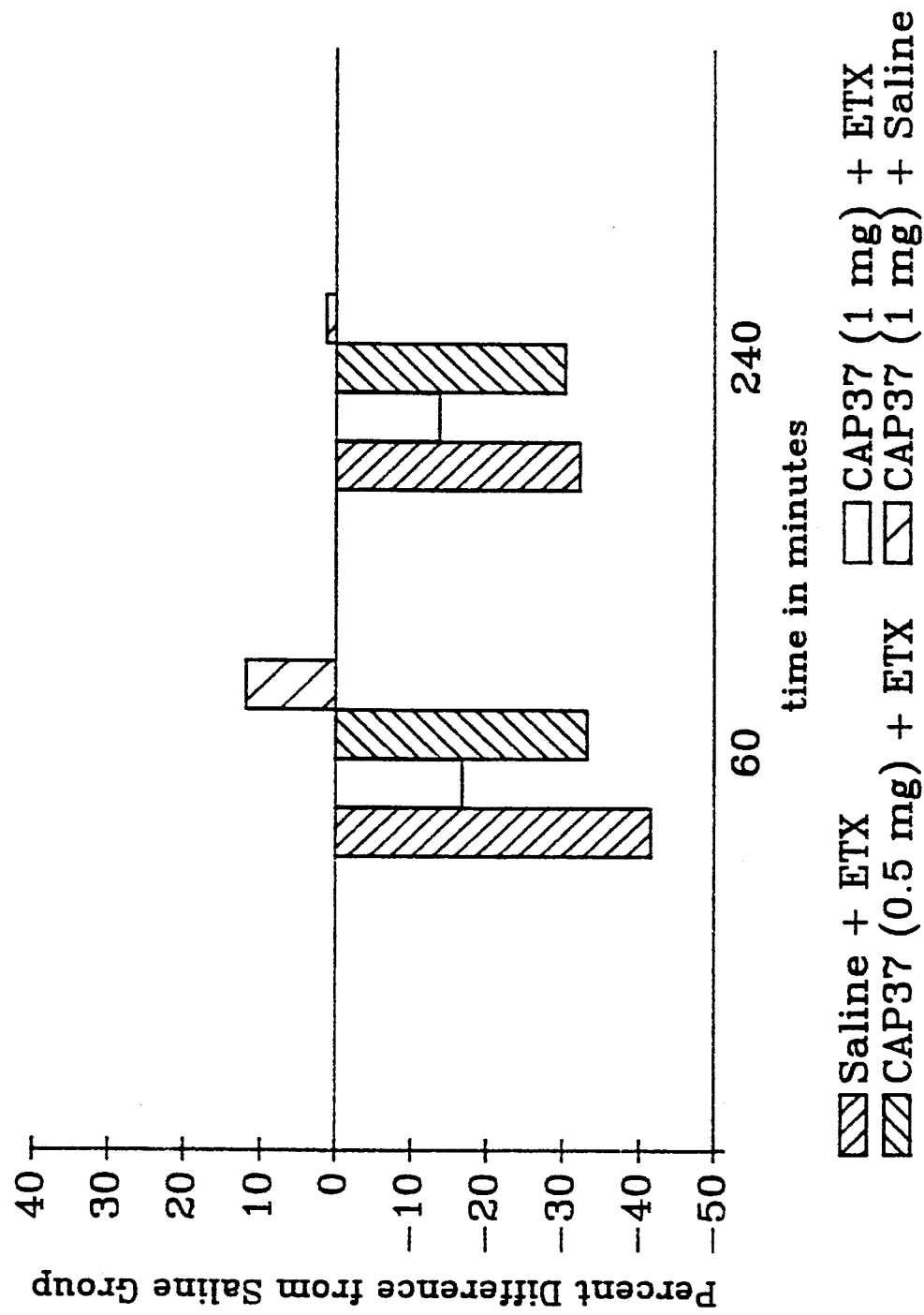
FIG. 6 is a graph comparing the effects of endotoxin and CAP37 peptide 20–44 on white blood cell count in the hyperdynamic model of septic shock.
Figure 7:
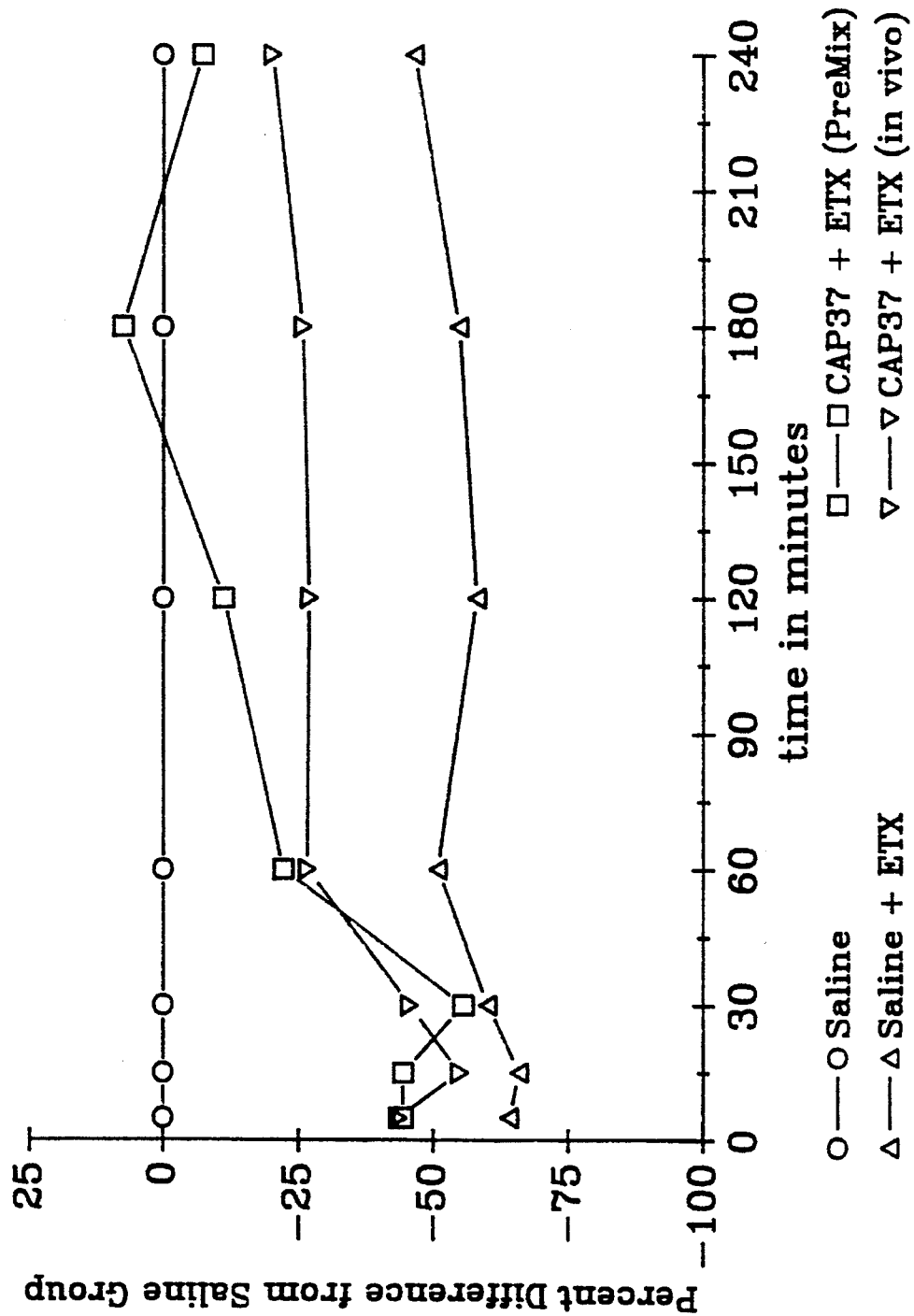
FIG. 7 is a graph comparing the effects of endotoxin and CAP37 peptide 20–44 on cardiac index in the hypodynamic model of septic shock.

Using a hyperdynamic model, the capacity of CAP37 peptide 20–44 to block or attenuate the in vivo effects of endotoxin (lipopolysaccharide B, E. coli 0127:B8, Sigma Chemical Co.) was evaluated by comparing the hemodynamic and metabolic responses of rats infused with 250 μg/kg of endotoxin over 30 minutes to that of rats which received the same dose of endotoxin that had been pretreated in vitro with 0.5 or 1.0 mg/kg of CAP37 peptide 20–44 prior to administration. This preliminary study contained five treatment groups: 1) saline (S)+endotoxin (ETX), 2) CAP37 peptide 20–44 (1.0 mg/kg)+ETX, 3) CAP37 peptide 20–44 (0.5 mg/kg)+ETX, 4) CAP37 peptide 20–44 (1.0 mg/kg)+ saline, and 5) saline. Each group contained 10 test animals. Control groups 4 and 5 were completely stable throughout the entire monitoring periods indicating the absence of a hemodynamic effect of CAP37 peptide 20–44 per se (see FIG. 4). In hyperdynamic shock, induced by an infusion of endotoxin (250 μg/kg) over a 30 minute time period, a 23% increase in cardiac index occurred within 30 minutes and an increase over the control was sustained for over one hour, falling to below the control value at 90 minutes, and remaining at about 20% below control for the remainder of the 4 hour monitoring period (FIG. 2). Systemic vascular resistance was essentially the mirror image of cardiac output, decreasing to about 20% of control at 30 minutes and sustaining an increase from 90 to 240 minutes reaching a peak of 40% of control at 180 minutes (FIG. 3). The response of cardiac stroke volume mimicked the cardiac output response (FIG. 4). Inadequate tissue perfusion was demonstrated by the significant increase in blood lactate concentrations indicating a shift from aerobic to anaerobic metabolism (FIG. 5). In the hyperdynamic model, injecting endotoxin into the animals has a major effect on cardiac index (FIG. 2), systemic vascular resistance (FIG. 3), and stroke volume (FIG. 4), but not on mean arterial pressure, heart rate, or respiration rate. There appears to be a slight increase in body temperature. Hematocrit and glucose concentrations were unaffected by endotoxin infusion. The circulating white blood cell count (FIG. 6) however, dropped dramatically with endotoxin infusion indicating an increase in the marginating pool and adherence to endothelial cells. The peptide 20–44 ameliorated the drop in white blood cell count. Of the parameters that changed following endotoxin infusion, it is apparent that infusion of CAP37 peptide 20–44, at the higher concentration had a preventive (or blocking) effect. There was no difference between the saline controls and the group receiving the high dose of peptide. All of these endotoxin-induced responses were greatly or completely prevented by the 1.0 mg/kg dose of CAP37 peptide 20–44 and the values for this group were similar to those of the two control groups. The lower dose of peptide (0.5 mg) was not as effective. The 0.5 mg/kg dose prevented the hyperdynamic phase, but not the transition to the hypodynamic phase, which occurred about 60 minutes after infusion. This suggests a dose-effect by CAP37 peptide 20–44.

Hypodynamic Model

Figure 10:
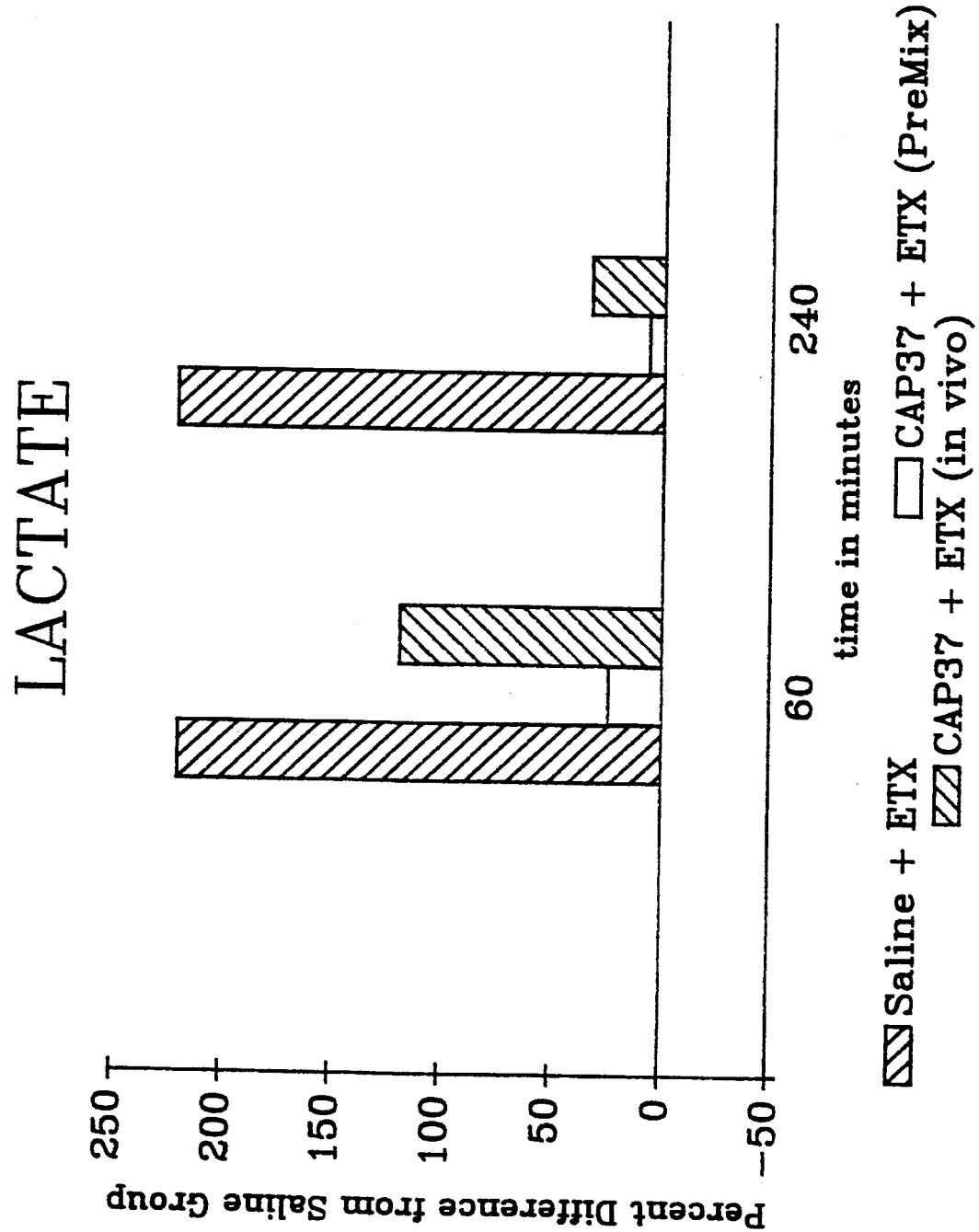
FIG. 10 is a graph comparing the effects of endotoxin and CAP37 peptide 20–44 on lactate concentration in the hypodynamic model of septic shock.
Figure 11:
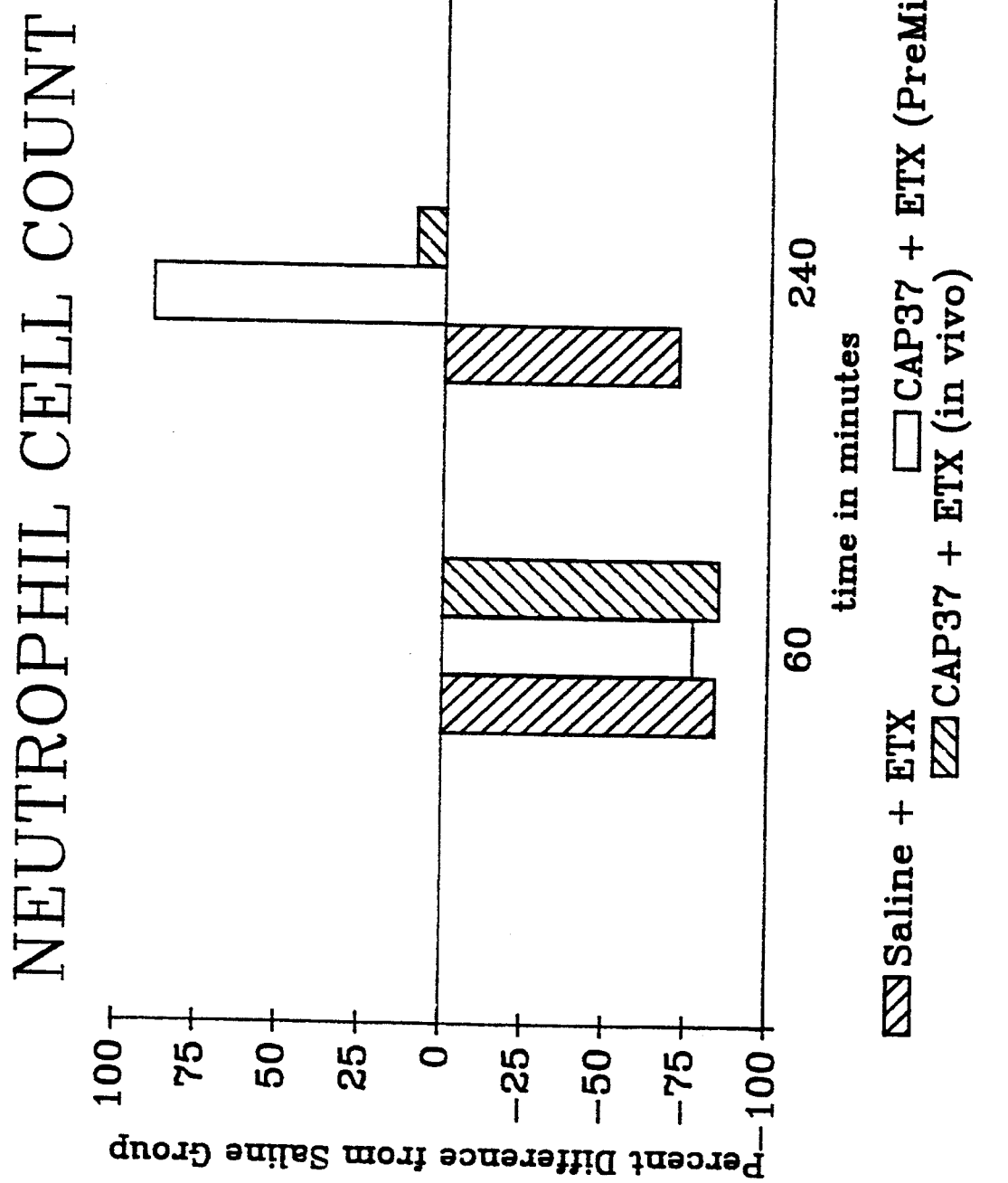
FIG. 11 is a graph comparing the effects of endotoxin and CAP37 peptide 20–44 on neutrophil cell count in the hypodynamic model of septic shock.

The ability of CAP37 peptide 20–44 to ameliorate the responses to larger doses of endotoxin (20 mg/kg) which induce hypodynamic septic shock is illustrated in FIGS. 7–11. The hypodynamic model uses an extremely high dose of endotoxin (20 mg/kg) and is given in a single bolus. This model is associated with the late stages of septic shock in the absence of fluid resuscitation. The 20 mg/kg dose is an LD90 dose, i.e. 9 of 10 animals were dead by 24 hr. Three groups were involved in this study: 1) saline 2) CAP37 peptide 20–44 (3.0 mg/kg) premixed with endotoxin before administration, 3) CAP37 peptide 20–44 infused in vivo simultaneously with endotoxin. Each group contained 5 animals. Endotoxin (20.0 mg/kg) delivered as a bolus (Group 1) elicited an intense sustained decrease in cardiac output (FIG. 7), an increase in systemic vascular resistance (FIG. 8), and a decrease in stroke volume (FIG. 9) suggesting a situation of inadequate tissue perfusion which was substantiated by significantly increased blood lactate concentrations (FIG. 10). An important characteristic of this model of endotoxic shock is a dramatic decrease in circulating neutrophils (FIG. 11) indicating margination and creating the potential for migration into the tissue. Both CAP37 peptide 20–44 treatments (Groups 2 and 3) significantly attenuated the cardiovascular disturbances and the increase in lactate concentrations which returned to or were maintained at near baseline levels. Circulating neutrophil counts had returned to normal by the end of the monitoring period in the peptide-treated groups. In this model of hypodynamic endotoxic shock a higher peptide concentration should increase the effectiveness. The results of these studies conclusively demonstrate that CAP37 peptide 20–44 has the capacity to inhibit or prevent the in vivo activity of endotoxin.

Methodology

Male Sprague-Dawley rats weighing 300±25 gms were used in this study as test animals. The rats were initially anesthetized with 5% enflurane and then intubated and connected to a rodent respirator delivering 2% enflurane. The right carotid artery was cannulated with a thermocouple-catheter combination for measurement of thermodilution cardiac output curves (Columbus Instruments, CardioMaxII-R) and aortic blood pressure and for sampling arterial blood. The thermocouple tip was placed in the aortic arch just distal to the aortic valve. The thermocouple-catheter combination was constructed by inserting a Columbus Instruments FR #1 microprobe into Tygon Micro Bore tubing (0.030 in. I.D., 0.090 in. O.D.) through a hole in the tubing wall. The microprobe was extended 1⅛ in past the end of the Micro bore tubing, and epoxy was applied to seal the hole and secure the microprobe. The microprobe was then passed through the proper length of Teflon tubing (lightweight, 24 ga) cut to allow the tip of the microprobe to extend just past the end of the Teflon tubing after the Teflon tubing had been wedged tightly into the end of the larger Tygon tubing.

The tip of one catheter (Silastic-Medical Grade tubing— 0.025 in. I.D., 0.047 in. O.D.) was placed just adjacent to the right atrium via the right jugular vein for injection of endotoxin (hypodynamic model; 20 mg/kg delivered as a bolus over 15 seconds)/treatment composition, monitoring central venous pressure, and rapid injection of room-temperature saline to produce thermodilution curves for calculation of cardiac output. Animals in the hyperdynamic model were implanted with two catheters. One catheter (Silastic-Medical Grade tubing—0.025 in. I.D., 0.047 in. O.D.) was placed just adjacent to the right atrium for monitoring central venous pressure, and to generate the thermodilution curves. An additional smaller catheter (Silastic-Medical Grade tubing—0.020 in. I.D., 0.037 in. O.D.) was also placed in the vein to deliver a continuous infusion of endotoxin (hyperdynamic model; 250 μg/kg infused over 30 minutes)/treatment composition. The proper distance for insertion of the venous and arterial catheters to achieve the optimal tip placement was determined in a series of experiments using anesthetized animals of the same sex and weight as those used in this study. At the end of each study in the conscious animals presented here, the catheters were checked visually to assure proper placement.

The catheters were guided under the skin exiting through the back of the neck just below the base of the skull. All incision areas were anesthetized (lidocaine) before surgery and again just before suturing. The animals were allowed to regain consciousness and were then placed in cages that allowed unrestrained movement about the cage at all times throughout the study with no further handling. Sixty minutes from recovery and thirty minutes before treatment, baseline control measurements were taken. Utilization of a swivel-cannulae system provided continuous measurements of central venous pressure, aortic blood pressure, and heart rate. The dose of endotoxin used for the hyperdynamic model was 250 μg/kg which was infused via a separate catheter placed in a jugular vein. The dose used for the hypodynamic model was 20 mg/kg. Cardiac outputs were measured using the thermodilution technique by rapidly injecting a volume calculated to deliver 100 μl of room temperature saline to the circulatory system. At the end of the 30 minute control period, the treatment composition was injected intravenously. Central venous and aortic blood pressures, heart rate and respiration rate were continuously monitored for the next 4 hours. Following the control readings, cardiac output measurements were made at 5, 15, 30, 60, 120, 180 and 240 minutes after treatment. Arterial blood samples were also taken for measuring TNF (Tumor necrosis factor) and IL-1 (interleukin-1), lactate, PMN counts and blood glucose.

Additional details concerning the methodology of the hypodynamic model may be found in the article by D. J. Brackett, C. F. Schaefer, P. Tompkins, L. Fagraeus, L. J. Peters, and M. F. Wilson which is entitled "Evaluation of Cardiac Output, Total Peripheral Vascular Resistance, and Plasma Concentrations of Vasopressin in the Conscious, Unrestrained Rat During Endotoxemia," *Circ. Shock* 17:273–284 (1985) which is hereby incorporated herein in its entirety by reference.

Utility

The present invention contemplates using peptide 20–44 and effective subunits thereof both to treat ongoing endotoxic shock and to prophylactically treat an individual who may have a risk of septic shock prior to a surgical procedure. The peptide would be delivered, in a preferred embodiment, intravenously.

The dose would be approximately 3 mg/kg body weight. The peptide would be suspended in a suitable carrier such as normal saline at a concentration of 1 mg/ml. Thus for the average 70 kg male, this would involve a volume of 210 ml. This should be given as one infusion, intravenously over 30–60 minutes. A second infusion, may be given at 24 hours after the first infusion. Subsequent infusions over the next 72 hours could be required in the event circulating endotoxin levels are still apparent. Antibiotics, intravenous fluids, cardiovascular and respiratory support could also be provided if requested by the attending physician in a manner known to one of ordinary skill in the art.

Changes may be made in the construction and the operation of the various components, elements and assemblies described herein or in the steps or the sequence of steps of the methods described herein without departing from the spirit and scope of the invention as defined in the following claims.

What is claimed is:

1. A method for treating septic shock, comprising administering a therapeutic composition comprising a pharmacologically effective amount of a bacterial lipopolysaccharide binding peptide having the amino acid sequence as defined in the Sequence Listing by SEQ ID NO:2.

2. A method for treating septic shock, comprising administering a therapeutic composition comprising a pharmacologically effective amount of a bacterial lipopolysaccharide binding peptide having the amino acid sequence as defined in the Sequence Listing by SEQ ID NO:1.

3. A method of prophylactic treatment for preventing or minimizing septic shock, comprising administering a therapeutic composition comprising a pharmacologically effective amount of a lipopolysaccharide binding peptide derived from CAP37 protein wherein the peptide derived from CAP37 has the amino acid sequence as defined in the Sequence Listing by SEQ ID NO:1 or by SEQ ID NO:2.

4. A method of treating physiological effects caused by bacterial lipopolysaccharide, comprising administering a therapeutic composition comprising a pharmacologically effective amount of a bacterial lipopolysaccharide binding peptide derived from CAP37 protein wherein the peptide derived from CAP37 has the amino acid sequence as defined in the Sequence Listing by SEQ ID NO:1 or by SEQ ID NO:2.

5. A method of treating the effects of bacterial lipopolysaccharide on systemic vascular resistance, cardiac output, tissue perfusion and white blood cell count, comprising administering a therapeutic composition comprising a pharmacologically effective amount of a peptide having the amino acid sequence as defined in the Sequence Listing by SEQ ID NO:1 or by SEQ ID NO:2.

6. A method of mediating or preventing the effects of a bacterial lipopolysaccharide-induced endotoxic response in a test animal, comprising:

providing a test animal;

administering a predetermined amount of endotoxin to the test animal; and administering a predetermined amount of a CAP37 peptide having the amino acid sequence as defined in the Sequence Listing by SEQ ID NO:1 or by SEQ ID NO:2 to the test animal.

* * * * *

UNITED STATES PATENT AND TRADEMARK OFFICE
CERTIFICATE OF CORRECTION

PATENT NO. : 5,607,916
DATED : March 4, 1997
INVENTOR(S) : Pereira et al.

It is certified that error appears in the above-indentified patent and that said Letters Patent is hereby corrected as shown below:

Column 1, line 15, please delete "Mar. 19" and substitute therefor --Mar. 18--.

Column 4, line 44, please delete "comprising".

Column 4, line 45, after "animal", please insert --comprising--.

Column 6, line 26, please delete "Peteira" and substitute therefor --Pereira--.

Signed and Sealed this

Seventeenth Day of June, 1997

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 20-44aa of mature CAP37 protein ( x i ) SEQUENCE DESCRIPTION: SEQ ID NO:1:

Asn Gln Gly Arg His Phe Cys Gly Gly Ala Leu Ile His Ala Arg Phe
1               5                   10                  15

Val Met Thr Ala Ala Ser Cys Phe Gln
            20                  25

( 2 ) INFORMATION FOR SEQ ID NO:2:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( v ) FRAGMENT TYPE: internal ( v i ) ORIGINAL SOURCE: 23-42aa of mature CAP37 protein ( x i ) SEQUENCE DESCRIPTION: SEQ ID NO:2:

```
Arg His Phe Cys Gly Gly Ala Leu Ile His Ala Arg Phe Val Met Thr
1               5                   10                  15
Ala Ala Ser Cys
            20
```